United States Patent [19]

Callaway

[11] Patent Number: 5,146,206

[45] Date of Patent: Sep. 8, 1992

[54] PATIENT AMBULATION MOTION DETECTOR WITH MULTIPLE SWITCH MOTION DETECTION

[76] Inventor: James J. Callaway, 1577 Moran Rd., Franklin, Tenn. 37064

[21] Appl. No.: 683,958

[22] Filed: Apr. 12, 1991

Related U.S. Application Data

[63] Continuation-in-part of Ser. No. 432,867, Nov. 7, 1989, Pat. No. 5,008,654.

[51] Int. Cl.$^5$ .................................................. G08B 23/00
[52] U.S. Cl. .................................. 340/573; 340/686; 128/782; 200/DIG. 2
[58] Field of Search ............... 340/573, 689, 686, 575, 340/568; 200/188, 220, 221, 61.52, 61.45 R, DIG. 2; 128/782

[56] References Cited

U.S. PATENT DOCUMENTS

| | | | |
|---|---|---|---|
| 2,713,159 | 7/1955 | Morrison | 340/689 |
| 4,179,692 | 12/1979 | Vance | 340/573 |
| 4,282,412 | 8/1981 | Florin | 200/61.52 |
| 4,348,562 | 9/1982 | Florin | 200/52 R |
| 4,536,755 | 8/1985 | Holzgang et al. | 340/573 |
| 4,583,084 | 4/1986 | Henderson et al. | 340/573 |
| 4,633,237 | 12/1986 | Tucknott et al. | 340/573 |
| 4,972,177 | 11/1990 | Nolan | 340/573 |

Primary Examiner—Jin F. Ng
Assistant Examiner—Christine K. Oda
Attorney, Agent, or Firm—Fleit, Jacobson, Cohn, Price, Holman & Stern

[57] ABSTRACT

A patient ambulation motion detector intended for attachment to a patient's body. The detector includes a motion sensor switch and a detachment detector switch which are mounted on a circuit board, the circuit board being in turn enclosed within an attachment casing which is attachable to a lateral surface of the patient's body. The motion sensor comprises three SPST mercury switches mounted to the circuit board and oriented so as to be responsive to declination of that portion of the patient's body to which the detector is attached and which declination is indicative of impending ambulation, but non-responsive to positions in which the posture of the patient is not indicative of impending ambulation. The detachment detector switch is a spring contact switch which is openable and closable by a plunger acting thereon and sensitive to detachment of the detector from the patient's body. The detector may be wired to a conventional switched nurse call system. When multiple mercury switches are employed, the switches are connected in series so as to prevent false alarms.

8 Claims, 5 Drawing Sheets

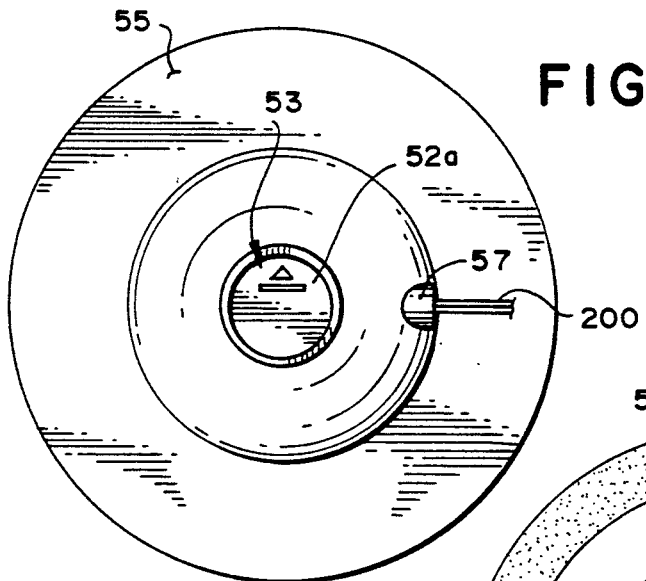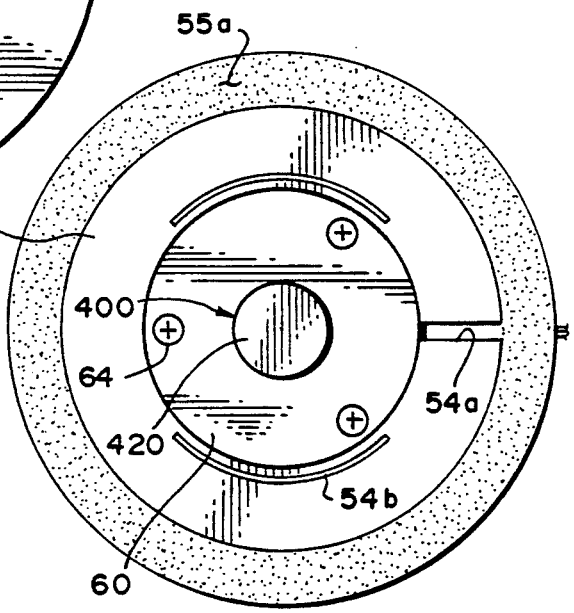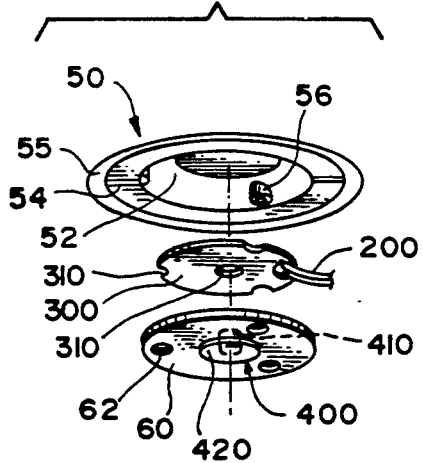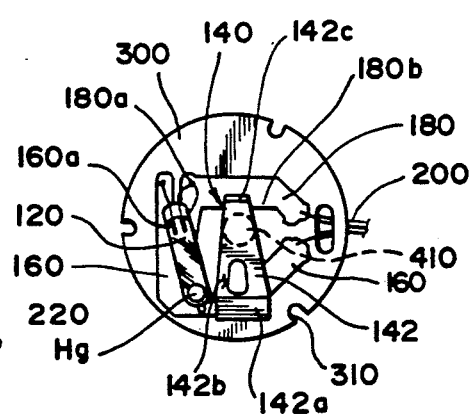

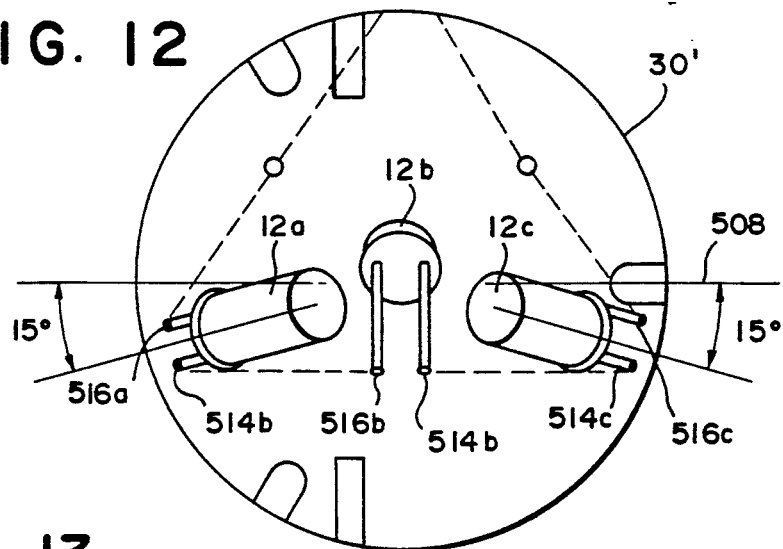
FIG. 12
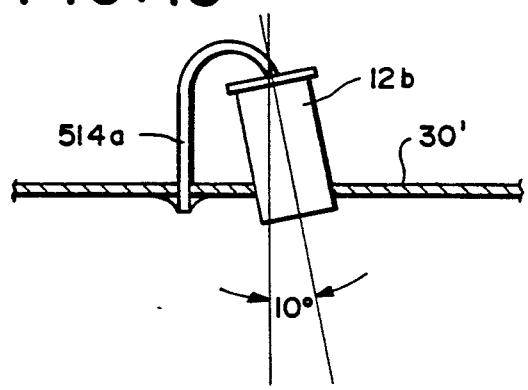
FIG. 13
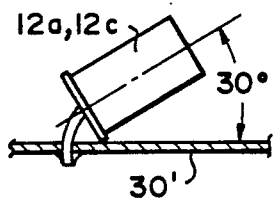
FIG. 14
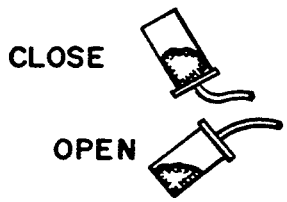
FIG. 15a
FIG. 15b
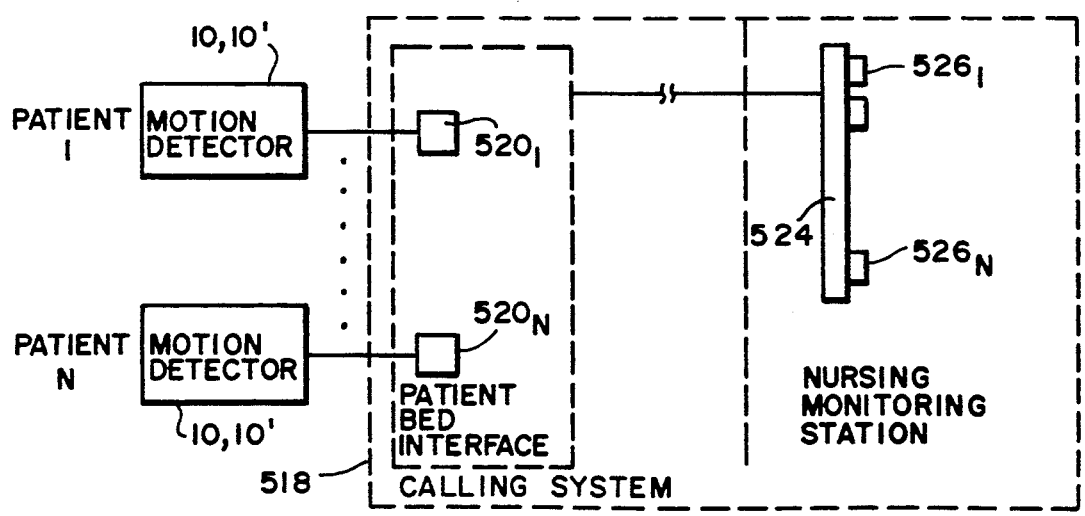
FIG. 17

PATIENT AMBULATION MOTION DETECTOR WITH MULTIPLE SWITCH MOTION DETECTION

PRIOR RELATED APPLICATIONS

This application is a continuation-in-part of U.S. patent application Ser. No. 07/432,867, filed Nov. 7, 1989, U.S. Pat. No. 5,008,654.

BACKGROUND AND SUMMARY OF THE INVENTION

The present invention relates generally to devices and methods for monitoring patient activity, and particularly to means for detecting the movement of a patient in a bed from a horizontal, i.e. prone or supine position to an erect or semi-erect position, as in an attempt by the patient to get out of bed preparatory to ambulation.

It is often desirable to ensure that hospital patients remain supine or keep to their beds, especially after and while recovering from surgery, and when bed rest is absolutely required. It is also often desirable for hospital personnel to directly monitor the physical activity of a patient without actually being in attendance at the patient's bedside, so as to be aware of any activity which may be deleterious to the patient's condition. Thus, it is often desirable to monitor a patient in order to detect, and therefore be able to avoid, the anesthetized patient, as upon partially regaining consciousness after coming out of surgery, getting out of bed (or making an attempt to do so) when such activity may place the patient, who may not be aware of his/her own condition, at risk. At the same time, the use of restraints is undesirable, for obvious reasons, making it necessary for attending personnel to personally monitor the patient's activity level in order to assure the patient does not make or undertake any movement which might jeopardize the patient's condition. Typically, it might be desired to guard against the patient getting out of bed, however such might not be detected by hospital personnel until the patient has actually done so. Thus, it is desirable for hospital personnel to be able to detect when the patient is attempting to, or in the process of alighting the bed preparatory to patient ambulation, and to alert the hospital personnel of this impending activity, so as to permit the hospital personnel to attend the patient before alighting and ambulation actually proceed. The present invention is directed to a means for making possible such early detection of patient movement indicative of impending patient ambulation.

More particularly, the present invention is directed to a device which attaches easily and unobtrusively to a lateral surface of the thigh or other portion of the body of a patient and which is sensitive to attitudinal changes in the orientation of the patient's thigh or body so that an alarm signal is produced thereby when the patient attempts to step out of bed preparatory to ambulation, this alarm signal preferably being transmitted over the "nurse's call" system for alerting attending health care personnel of the patient's activity. Additionally, the device provides an alarm signal if it is removed or becomes dislodged from the patient. Advantageously, the alarm signal remains on until reset at the device, in distinction to a normal nurse call signal which may be cancelled at the nurse's station console, thus indicating to attending personnel that the alert signal is from the patient ambulation motion detector device and not simply a nurse call signal.

The patient ambulation detector device of the present invention is self-attaching and is adapted for attachment to either the right or left thigh or to the upper body of the patient as appropriate. The device is compact, simple in construction and relatively inexpensive to manufacture. Further, the device can be easily connected to existing nurse call systems, without electrical or mechanical system modification.

A number of devices for monitoring bed-patient movement have been previously proposed. One such device is disclosed in U.S. Pat. No. 4,536,755 of Holzgang et al., and includes a mercury switch mounted on a circuit board and constituting an angle inclination sensing means for sensing angular displacement of a patient's upper leg relative to a reference datum plane. In this prior device, the circuit board with the mercury switch mounted thereon is housed in an enclosing carrier module which is strapped to the patient's thigh by means of an elastic band so as to be positioned on the anterior, i.e. upper surface of the patient's thigh, i.e. femur. An adhesive-backed foam pad is attached to the rear wall of the carrier module to serve as an interface between the patient's thigh and the module, to secure the device in place without detriment to patient comfort. In order to detect the unauthorized removal of the device from the patient's thigh, the device also includes a pressure switch having contacts which project from the lower surface of the circuit board and extend through an aperture in the carrier module rear wall to engage the anterior surface of the patient's thigh. Sensing of the downwardly directed angular inclination of the distal end of the patient's femur is accomplished by orienting the mercury switch on the circuit board so that, when the device is secured to the patient's thigh, an upwardly or downwardly directed angular inclination of the femur portion of the patient's leg proximal the knee has the effect of adjusting the position of the mercury contained in the switch. In this way, a downwardly directed inclination of the patient's leg which exceeds a preselected inclination threshold angle will bring the mercury within the switch casing into contact with a pair of respective electrodes to form a closed conduction path therebetween, effecting closure of the switch and applying battery voltage to a time delay circuit and thence to the gate electrode of an SCR, thereby switching the SCR on. When switched on, the SCR supplies current to an alarm circuit oscillator stage which generates audio frequency tone bursts which are applied to an audio transducer for producing an audible signal to indicate to attending personnel that the patient is in an "ambulatory enabling" position. Unauthorized removal or dislodgement of the device from the patient's thigh causes the pressure switch to close, which in turn causes immediate sounding of the audible alarm signal.

This prior device has only limited usefulness, for several reasons. Being battery powered, it is susceptible to becoming inoperative due to the battery running out. Additionally, the device only produces an audio alarm signal from the self-contained audio transducer, which alarm signal may not be audible to hospital personnel located, for example, at a nurse's station some distance from the patient's room, especially if the door to the patient's room is closed. Further, the audio alarm may not be audible above or distinguishable from background and other noise, such as paging messages, in the hospital ward. It is suggested that a radio transmitter might be substituted for the audio transducer to produce an inaudible warning signal for reception at a remote location. However, such a system is still susceptible to inoperability due to a partially or completely discharged battery, and requires the additional expense of installing reception means at each necessary location for alerting the responsible attending personnel.

Another prior device of this type which utilizes a specially configured mercury switch position sensor is disclosed in U.S. Pat. No. 4,348,562 to Florin. This disclosed device is described to provide an alarm system which is capable of being integrated with existing hospital call systems so as activate a patient's call light and/or buzzer, thereby notifying the nurse of the exact location of the patient at risk. Such integration with existing call systems would be advantageous also in that no additional power supply would be required.

This prior device monitors changes in position from the horizontal of the anterior surface of a patient's chest or thigh towards a more vertical orientation which may signify impending injury due to a fall or rising of the patient. The device uses a particularly configured special mercury switch casing designed with a large head chamber, in which a mercury ball normally resides, connected via an axial throat passage to a smaller foot chamber wherein are provided spaced-apart electrodes. Basically, the head chamber and its transition region with the connecting throat passage are so configured as to prevent the mercury passing into the throat passage until the angle of inclination of the anterior body surface of the patient to which the device is attached exceeds 70° from the horizontal, while the foot chamber is made deep, so that once the mercury has moved down into the foot chamber and switch closure has thereby been effected the mercury is prevented from flowing back out of the foot chamber into the throat passage and opening the switch until the switch assembly is inverted to a 90° head-down position for thus resetting the device.

This described prior device is fashioned by forming the chambers and connecting passage in a plastic block into which are led connecting wires the ends of which are bared and particularly disposed in the foot chamber for providing the switch contacts, with closure lids being fastened atop and below the block. A removable adhesive is applied to the bottom surface of this assembly in order to prepare it for application to an anterior horizontal surface of the patient. However, this prior device also has limited usefulness, due in part to the cost and complexity of fabricating the specially configured chambers and connecting passage. Also, both this prior device of Florin and the previously noted prior Holzgang et al. device are both required to be positioned on an anterior surface of the patient's body for obtaining therefrom a horizontal plane datum, and are consequently obtrusive. Further, in practice the disposition of the anterior surfaces of a patient's body may not in fact lie on the horizontal but rather may tend to be more or less inclined when the patient is lying in bed, and will naturally tend to move inclinedly along with normal body movements as during breathing. Also, it may be the case that portions of the patient's body, and hence its anterior surfaces, are intended to be inclined or reclined for various reasons such as to promote drainage, assist respiration or maintain traction or flexure, in which case a monitoring device which necessarily requires attaching at an anterior horizontal body surface may not be at all suitable.

The sensing of the patient's physical position and movement with an ordinary gravity mercury switch used as a motion detector is advantageously convenient, as ordinary mercury switches are small, sensitive and widely available at reasonable cost. However, when a mercury switch type device is designed to be attached or positioned on an anterior, i.e. horizontal portion of the supine patient's body, it become necessary to orient the ordinary mercury switch itself generally vertically inclined or upright in order to be sensitive to vertical inclination movement relative the horizontal datum plane, and thus the device enclosure must be made sufficiently large to accommodate the height of the generally vertically oriented mercury switch bulb, making the device bulky and obtrusive, or a specially configured custom mercury switch must be utilized as in the noted Florin device having the mercury switch in a generally horizontal disposition, in order to obtain a lower height aspect while remaining insensitive to normal slight motion about the horizontal datum.

Other prior devices for monitoring patient movement or for providing an alarm upon impending vacating of the bed by the patient are known from U.S. Pat. Nos. 4,179,692 to Vance; 4,583,084 to Henderson et al.; and 4,633,237 to Tucknott et al.

The present invention, in accordance with a first embodiment, provides a patient ambulation motion detector device of the mercury switch type which overcomes the limitations of the conventional devices, and which is unobtrusively positionable on a lateral surface of the patient's body, whereby it is made possible to utilize a generally vertically inclined ordinary mercury switch in such a device for reliable detection of patient body motion relative the horizontal datum plane. According to the first embodiment, the present invention provides a patient ambulation motion detector of the mercury switch type which is of simple design, having only three electrical components, one for sensing patient motion, one for detecting detachment of the device and one serving for mounting and interconnecting the other two, and which is connectable to conventional hospital nurse call systems.

According to a second embodiment, the present invention provides a motion detector having three motion single pull/single throw (SPST) detection mercury switches. The three mercury switches are electrically connected in series and each is arranged in a predetermined geometric orientation so as to minimize false alarms. Specifically, a centrally mounted switch detects relative vertical position and two adjacently mounted switches are provided to prevent unwanted alarm activation caused by the patient rolling over in bed to either side.

The above and other objects and advantages of the present invention will become more readily apparent from the following detailed description taken with reference to the accompanying drawings.

BRIEF DESCRIPTION OF THE DRAWINGS

FIG. 4 is a top view of the device embodied in accordance with the present invention.

FIG. 5 is a bottom view of the device embodied in accordance with the present invention.

FIG. 6 is an exploded view of the device embodied in accordance with the present invention.

FIG. 7 is a plan view showing the electrical component arrangement of the device embodied in accordance with the present invention.

FIG. 12 is an enlarged top view of the circuit board illustrating the relative geometrical orientation of the mercury switches.

FIG. 13 is an enlarged side view illustrating the mounting orientation of a central one of the mercury switches.

FIG. 14 is an enlarged side view illustrating the mounting orientation of the mercury switches positioned adjacent the central switch illustrated in FIG. 13.

FIGS. 15a and 15b are side views illustrating the close and open positions, respectively, of the mercury switches.

FIG. 17 is a block diagram illustrating the interconnection of a motion detector according to the present invention to a nurse calling system.

DETAILED DESCRIPTION OP THE INVENTION

Figure 1:
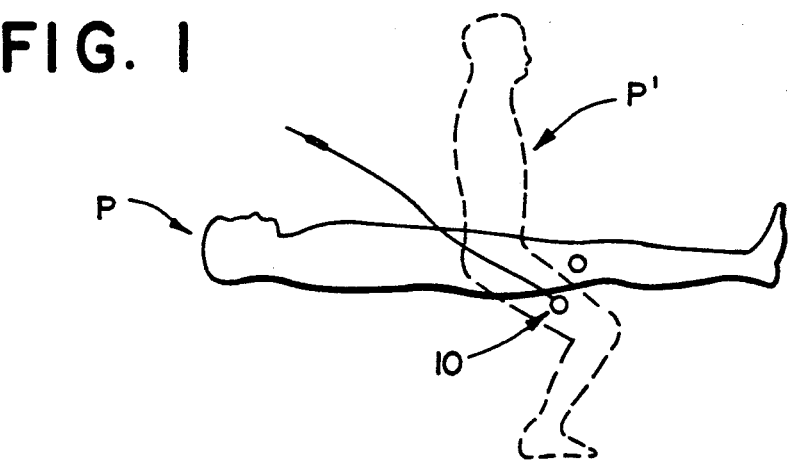
FIG. 1 is a pictorial representation showing a device in accordance with the present invention in use.

Referring now to FIG. 1, there is shown by the solid line and viewed from the right side, the outline of a person such as a hospital patient designated generally at P laying down in a supine generally horizontal position. The position of the patient P, having assumed a generally upright position with the upper torso raised to a generally vertical orientation and with the right leg inclined generally downwardly as in stepping from a bed prior to ambulation, is depicted generally by the dashed or broken line outline at P'.

Shown positioned on the outer lateral surface of the right thigh of the patient P, P' is a patient ambulation motion detector device according to the invention, designated generally at 10.

Figure 2:
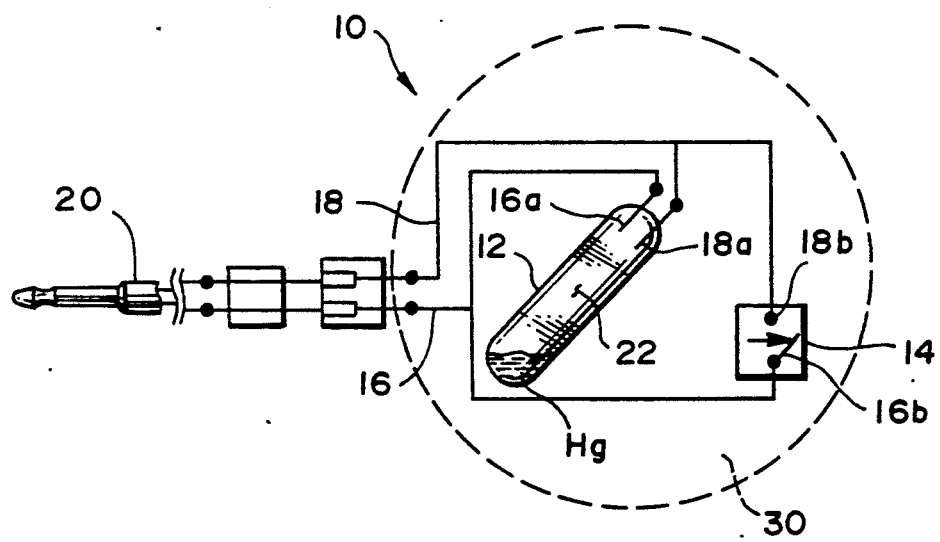
FIG. 2 is a schematic circuit diagram of a device in accordance with the present invention.

Referring now to FIG. 2, there is shown in partial schematic and partial pictorial form an electric circuit of the device 10 embodying the invention. Within the circular dashed outline (representing a printed circuit board and enclosure as detailed below) there is shown a parallel circuit of an SPST glass bulb/tube type mercury switch 12, which serves as the motion detector means of the device, and another SPST switch 14, which serves as the detachment detector means of the device, connected across a pair of respective signal/supply lines 16 and 18 which lines 16, 18 may, for example, be brought out to the tip and ring terminals of a phone-type plug 20. As shown, either the SPST mercury switch 12 or the other SPST switch 14 will, when made closed, connect the lines 16 and 18 with one another into a current or voltage loop, and effectively connecting the tip and ring of plug 20.

It should be noted that in FIG. 2 the mercury switch 12 is depicted with the axis of the tube 22 thereof oriented in a substantially vertical position, that is, inclined with respect to the horizontal bottom edge of the page, such that the electrodes 16a, 18a (connected to lines 16 and 18, respectively) are located at the higher, i.e. upper end of the tube 22 of the mercury switch 12 while the mercury Hg resides under the influence of gravity in the lower, i.e. bottom end of tube 22 away from electrodes 16a, 18a. Now considering the circular dashed outline in FIG. 2 as representing a printed circuit (i.e. PC) board 30 on which the lines 16, 18 and the switches 12, 14 are provided, it will be understood that this circuit board 30 lies on the vertical plane, i.e. parallel to the vertical plane of the page, and that the mercury switch 12 is depicted with the axis of the tube 22 also lying on the vertical plane parallel with the circuit board 30. In practice, it may be desirable to mount mercury switch 12 to circuit board such that the upper electrode end of the tube 22 is raised or spaced away slightly from the circuit board with the lower mercury-residing end of tube 22 close to or contacting the circuit board, thus inclining the upper electrode end of tube 22 upwardly with respect to the lower mercury-residing end relative to the circuit board 30, for reasons which will be made apparent below.

It may further be considered that the lines 16 and 18 depicted in FIG. 2 may be formed as conductor traces provided on circuit board 30, and an implementation of the circuit of FIG. 2 embodied on a circular circuit board 300 in accordance with the invention is shown in FIG. 7. On circuit board 300 there are provided conductor traces or lands 160, 180 corresponding to lines 16, 18 and connected to respective conductors of line cord 200. An SPST mercury switch 120 is mounted on circuit board 300 and has its upper end electrodes 160a, 180a connected to the conductor traces 160, 180 so that a connection between conductors 160 and 180 may be made by mercury Hg bridging the electrodes 160a, 180a of switch 120 when the circuit board 300 is rotated a sufficient number of degrees in the plane parallel to the page to cause the "ball" of mercury Hg to flow by gravity to the electrode end of the switch 120, i.e. when the electrode end of switch 120 is displaced so as to be in a lower position than the opposite mercury-residing end.

It will be recognized also that the mercury switch will be made closed whenever the circuit board is sufficiently displaced about the horizontal axis, i.e. made substantially perpendicular relative the plane of the page along a horizontal axis so as to bring the electrode end lower than the other end of the mercury switch, in which case the ball of mercury Hg will also be caused to flow to the electrode end and to bridge the electrodes 160a, 180a.

It will be appreciated therefore that if the device 10 incorporating the circuit board 30 (300) having the mercury switch 12 (120) mounted thereon is in turn positioned for example with the circuit board oriented flat upon, i.e. parallel with the side or lateral portion of a patient's thigh, i.e. on a substantially vertical surface of the patient's thigh as depicted in FIG. 1, then declination of the patient's thigh relative the horizontal, as upon the patient extending the thigh toward the floor in stepping from a bed preparatory to ambulation, will bring the electrode end of the mercury switch 12 (120)

increasingly lower relative the mercury-residing end until, due to increasing declination of the patient's thigh and the device 10 therewith, the mercury Hg is caused by gravity to flow to the electrode end of the switch tube and to bridge the electrodes 16a, 18a (160a, 180a), making the mercury switch closed and connecting the lines 16 and 18 (160, 180).

It will also be appreciated that the device 10 positioned thusly on the lateral surface of the patient's thigh will also be responsive to the patient rolling over onto his/her side, because such motion will tend to bring the ends of the mercury switch tube more or less level with one another, which may cause the mercury to spread out along the lower margins of the tube 22 (220) and which might allow the mercury Hg to contact the electrodes 16a, 18a (160a, 180a). In this case, it may be advisable to mount the mercury switch to the circuit board with the electrode end of the mercury switch tube 22 (220) raised slightly from the circuit board with respect to the mercury-residing end of the switch tube in order to prevent the mercury reaching the electrodes when the patient is laying on his/her side. On the other hand, it may be desired to detect when the patient is on his/her side, in which case the mounting of the mercury switch such that the electrodes 16a, 18a (160a, 180a) are oriented substantially on the same plane and parallel with the circuit board 30 (300) (and thus parallel with the patient's side) will permit the mercury to flow along the bottom of the switch tube 22 (220) and to contact and conductively bridge the electrodes for making the switch closed whenever the patient rolls onto his/her side such as to bring the axis of the tube 22 (220) parallel to the horizontal thus enabling sensing of such patient position.

There is also provided on the circuit board a second SPST switch designated generally at 140 which may advantageously take the form of a pressure or plunger switch by means of which the switch 140 may serve to sense detachment of the device 10 from the patient. Switch 140 includes a conductive spring contact member 142 (corresponding to the movable switch contact 16b in FIG. 2) which may for example be of beryllium-copper and is mounted at a base end 142a thereof to the circuit board 300. The base end 142a is electrically connected to conductor land 160. Spring contact member 142 also includes a medial bridge portion 142b which is at a higher level relative the circuit board 300 than is the base end 142a, being for example formed by imparting an S-bend in the member 142 between the base end portion 142a and medial bridge portion 142b, which form also imparts a spring action to the medial bridge portion 142b allowing it to bend relative the circuit board 300.

The other, free contact end 142c of conductive spring member 142 is bent downwardly towards the circuit board 300 so as to normally be urged, due to the aforementioned spring action of the medial portion 142b, into contact with an underlying portion of conductor land 180b (corresponding to the stationary switch contact 18b in FIG. 2). Thus, switch 140 is spring biased to a "normally closed" (NC) condition, whereas mercury switch 120 may be considered to function as a "normally open" (NO) type switch.

As shown in FIG. 6, a central hole is formed through circuit board 300, in a location underlying the medial bridge portion 142b of conductive spring member 142, in order to accommodate the passage therethrough of the shaft end 410 of a plunger member 400. Shaft end 410 abuts the underside of the bridge portion 142b as shown in dashed outline in FIG. 7. At its other end, plunger member 400 is provided with a pressure plate or flange 420, whereby force may be imparted to the plunger member 400 for pressing the shaft end against the bridge portion 142b of member 142 so as to lift the medial bridge portion 142b, and the free contact end portion 142c therewith, relative the circuit board 300, against the spring force of the member 142. In this way, pressure force on the pressure plate end 420 of plunger 400 exceeding the spring force of member 142 will cause the free contact end 142c of member 142 to be lifted out of contact with conductor land 180b for thereby breaking or opening the electrical connection between lines 160 and 180.

In practice, with the device 10 attached or held fast to the patient P, the plunger 400 will normally be pressed inwardly by the contact between the patient's body and the pressure plate end 420, and the spring force of member 142 in combination with the surface area of pressure plate end 420 are so selected as to enable such pressure force on the plunger 400 to easily lift the free contact end 142c of member 142 out of electrical connection with conductor land 180b, whereby the switch 140 is made open so long as the device 10 remains firmly attached or held fast to the patient's body. It will thus be appreciated that the switch 140 serves to sense detachment or removal of the device 10 from the patient by connecting the line 160 with line 180 for closing the circuit, while maintaining the circuit open so long as the device 10 remains in place on the patient.

The circuit board 300 may conveniently be accommodated within a housing or enclosure formed of an upper casing 50 and a lower casing 60 as shown in FIG. 6, by means of which attachment of the device 10 to the patient P may be facilitated. Conveniently, the casing may be of molded plastic construction, and should in any case be of electrically insulative material.

Figure 3:
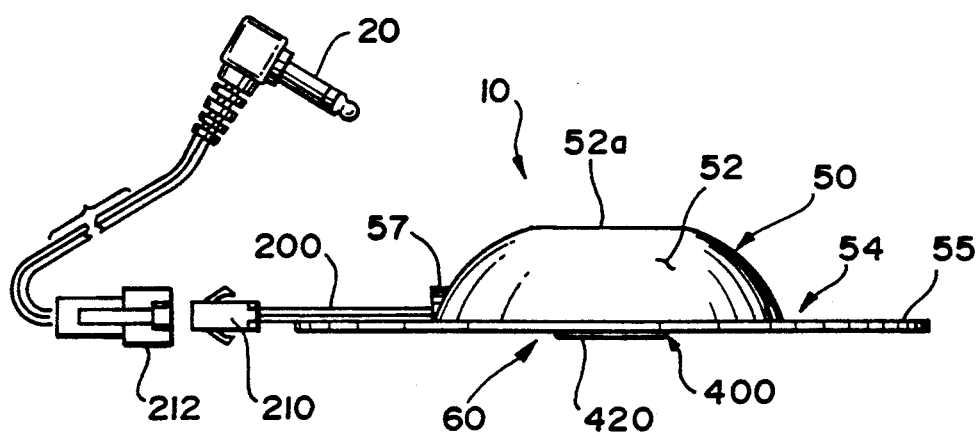
FIG. 3 is a side view of a device embodied in accordance with the present invention.

Referring now also to FIGS. 3 through 5, the upper casing 50 includes a shallow dome or inverted bowl-shaped central portion 52 from a lower margin of which extends radially outwardly a lip portion 54. The central portion 52 is sized adequately to accommodate the circuit board within its open interior, and thus may be quite shallow in depth from its lower margin to a flattened apex portion 52a since, in distinction to the aforementioned prior device of U.S. Pat. No. 4,536,755, the mercury switch in the present invention does not need to be inclined vertically from the circuit board and therefore presents only a minimal height aspect to be enclosed.

The open lower margin of central portion 52 is closed by the lower casing 60, the circuit board 300 being mounted fast therebetween. This may be accomplished by providing recesses 310 in the outer edge of circuit board 300 in register with threaded bosses 56 formed on the inner surface of central portion 52 of upper casing 50 and holes 62 formed through lower casing 60, whereby the upper casing 50 and lower casing 60 with the circuit board 300 therebetween may be fastened together with screws 64 inserted through the holes 62 and recesses 310 and engaging the bosses 56. As may be seen from FIG. 3, the lower casing 60 is flush with the lip portion 54 of the upper casing 50. Also, the lower casing 60 is provided centrally therethrough with a hole in register with the central hole in circuit board 300, for accommodating passage therethrough of the shaft portion 410 of plunger 400, while the underside of lower casing 60 serves as a rear abutment stop of the pressure plate 420 for limiting the inward movement of plunger 400. The plunger 400 may be retained in the lower casing 60 by, for example, a retaining clip inserted in a groove of the plunger shaft (not shown) between the lower casing 60 and circuit board 300 in order to prevent the spring force of member 142 from forcing the plunger 400 out too far.

The lip portion 54 of upper casing may be provided with a groove for accommodating passage of the line cord 200. Lip portion 54 is preferably made progressively thinner, i.e. tapered from its inner edge to its outer peripheral edge as to be flexible so as to conform at its peripheral portion with the curvature of the thigh lateral surface, and to this end lip portion 54 may include upper and lower arcuate cuts 54b formed therein proximate the lower margin of central portion 52 to facilitate flexing and curving of the lip portion 54 around the lateral thigh surface of the patient.

The flat top 52a of the upper casing 50 may be provided with indicia 53 thereon, for example an arrow or other marking pointing "up" to guide the proper placement of the device 10 on the lateral surface of the thigh with proper orientation of the mercury switch motion sensing means for responding to patient motion indicating impending ambulation. In this regard, it will of course be understood that "up" in this sense means that orientation of the device when attached to a lateral surface of the patient's thigh (or other body portion) which accordingly orients the mercury switch in an open state with the patient supine as described above, but which orients the mercury switch in a closed state when the patient's thigh is extended downwardly and inclined from the horizontal (or the patient's upper torso is raised up) as when stepping from a bed preparatory to ambulation.

For attaching the device 10 firmly to the patient's body, a thin flat flexible annular or ring-shaped attachment member 55 such as of foam or film sheet and having adhesive on a bottom side thereof is placed over the upper surface of lip portion 54 of upper casing 50 so as to be adhered thereto, and has an outer margin 55a which extends radially outwardly of the lip portion 54 as shown in FIG. 5, whereby this adhesive coated bottom surface of outer margin 55a is substantially flush with the undersides of lip portion 54 and lower casing 60.

Attachment member 55 is open at its center to allow the central portion 52 of upper casing 50 to project therethrough, and serves by the adherent fixation of its adhesive lower surface to the upper surface of lip portion 54 and radial extension outwardly thereof for adherently attaching the lip portion 54 and thus the device 10 proper flush to the surface of the patient's body with a degree of fixation between the device 10 and the patient's body sufficient for forcing the plunger inwardly against the spring force of member 142 to open the switch 140.

Thus, it is only necessary to "stick" the device firmly against the patient's body so as to adhere the exposed peripheral margin of the adhesive underside of attachment member 55 to the patient's body, in order to obtain a large circular contact area therebetween over which contact area a substantial yet unobtrusive adhesion force is obtained for firmly, closely and adherently attaching the device to the patient.

The line cord 200 carrying lines 160 and 180 from circuit board 300 may conveniently be passed through a groove 54a of lip portion 54 and through a strain relief 57 in central portion 52 of upper casing 50, to be connected in known manner to a conventional nurse call connector (FIG. 17) at the patient's bedside, for example by means of the phone plug 20 which will be plugged into a corresponding phone jack of a nurse call circuit. Line connectors 210, 212 may be provided in line cord 200 in known manner for permitting disconnection of device 10 from the plug portion f line cord 200.

FIGS. 8-16b illustrate the motion detector device 10' according to the second embodiment of the present invention.

Figure 8:
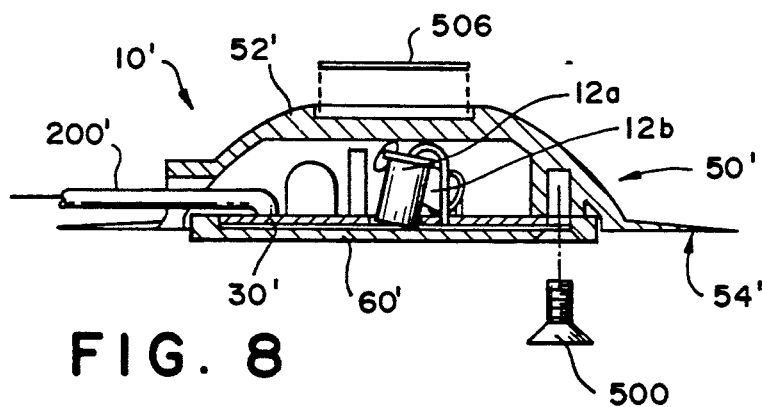
FIG. 8 is a side view, partially in section, of a motion detector in accordance with a second embodiment of the present invention.
Figures 9, 10:
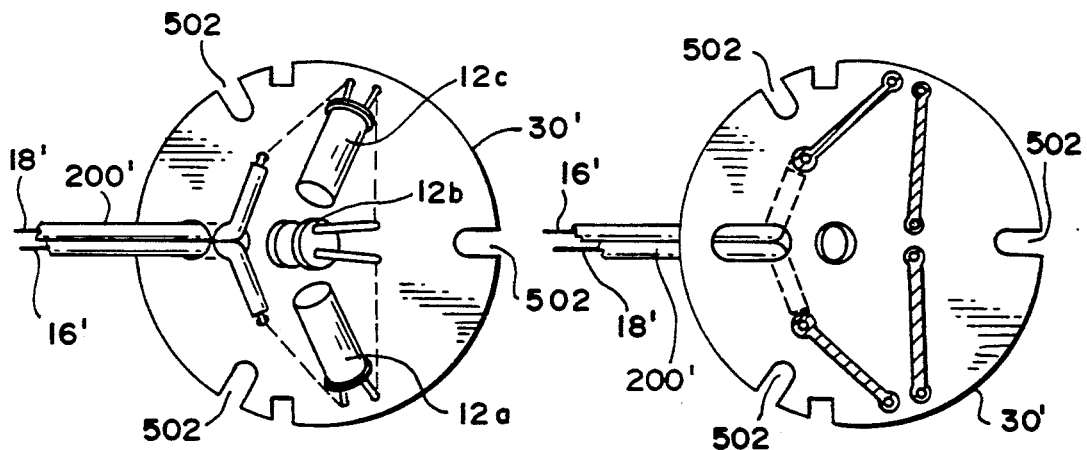
FIG. 9 is a top view of the circuit board illustrating three mercury switches in accordance with the second embodiment of the present invention.
FIG. 10 is a bottom view of the circuit board illustrating the solder connections of the mercury switches.

Referring first to FIGS. 8-10, the motion detector 10' is similar to motion detector 10 with the primary difference being the provision of multiple SPST mercury switches 12a, 12b, and 12c. Parts which are identical to those of motion detector 10 are assigned the same reference number with a prime. Switches 12a, 12b and 12c are of the same type as switch 12 of motion detector 10 and are arranged on the circuit board 30' in a predetermined orientation so as to maximize the accuracy with which detection is made. The switches are mounted on the circuit board 30' and electrically connected in series by solder connections on the bottom of the circuit board 30' (FIG. 10). Similar to motion detector 10, the lower casing 60' attaches to the bowl-shaped central portion 52' via a screw 500 through each of three holes in the lower casing 60'. In this regard, indented portions 502 are provided at each of the positions on the circuit board 30' corresponding to passage of the screws 500. In addition, a cut-out 504 is provided on the bowl-shaped casing 52' for receiving an emblem or label 506.

Figure 11:
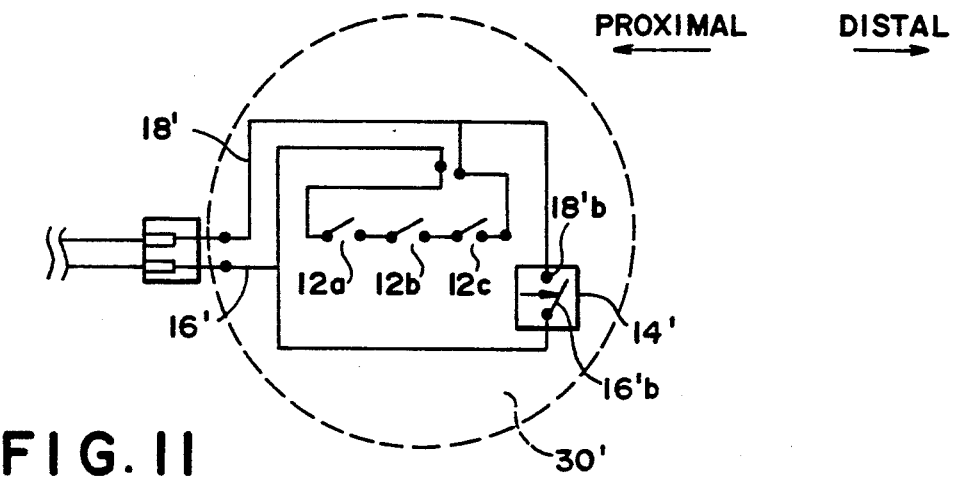
FIG. 11 is a schematic diagram illustrating the three switch motion detector circuit according to the present invention.

FIG. 11 illustrates the manner in which the mercury switches 12a, 12b and 12c are connected in relationship to the associated circuitry. Specifically, switches 12a, 12b and 12c are electrically connected in series, as shown, so that all of the switches must be closed to activate the remote alarm. Switch 14' operates in the same manner as switch 14 of motion detector 10. Lead lines 16' and 18' connect to the switches 12a, 12b and 12c so as to provide a completed circuit only when all of the switches 12a, 12b and 12c are closed or when switch 14' closes. Furthermore, the motion detector 10' is capable of being implemented without the use of the removal detector switch 14'.

In accordance with the second embodiment of the present invention, it is envisioned that the motion detector 10' is more versatile than motion detector 10. Specifically, the motion detector 10' may be attached to the upper leg (thigh) of a patient so as to detect when a patient attempts to get out of bed, or the detector 10' may be attached to the upper anterior chest for detecting when the patient sits up in preparation for getting out of bed. In addition, by providing multiple mercury switches, false alarms are minimized. Particularly, the switches 12a, 12b and 12c are three-dimensionally oriented on the circuit board 30' so as to prevent false alarms when a patient rolls to either side or makes any other move other than lowering the distal end of the detector 10' while elevating the proximal end of the detector 10'.

Figure 16A:
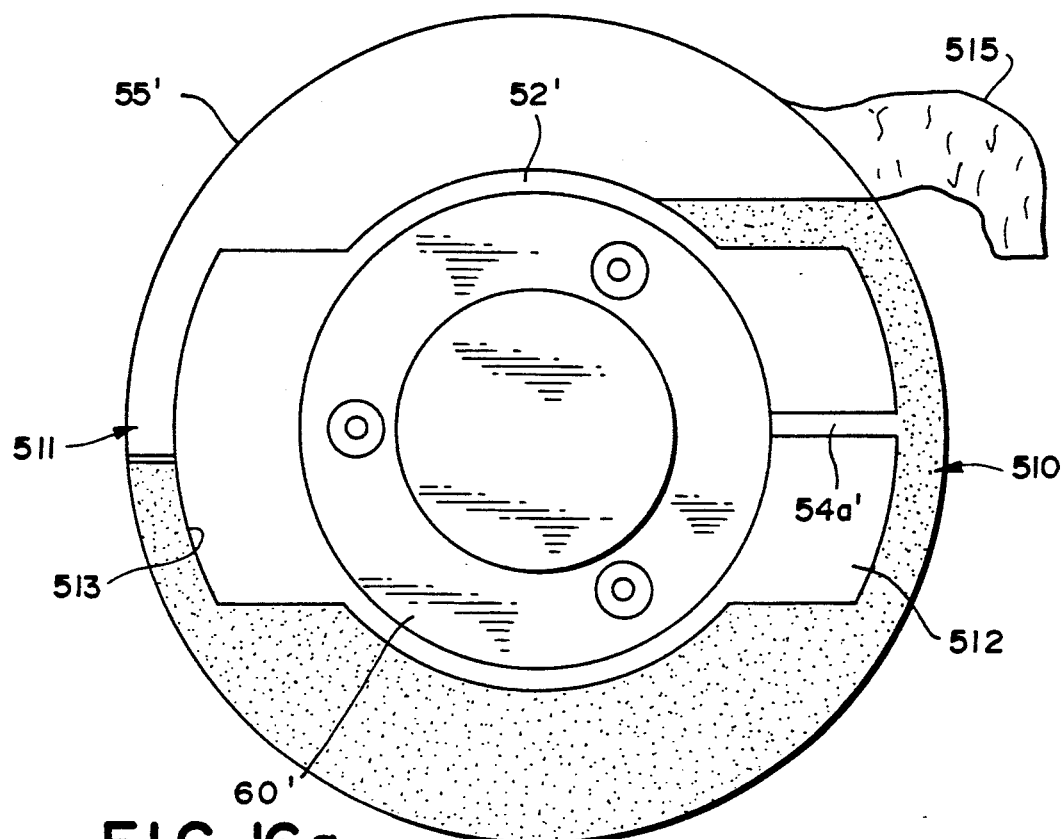
FIGS. 16a and 16b are bottom and top views, respectively, of the motion detector with its adhesive attachment pad secured thereto.
Figure 16B:
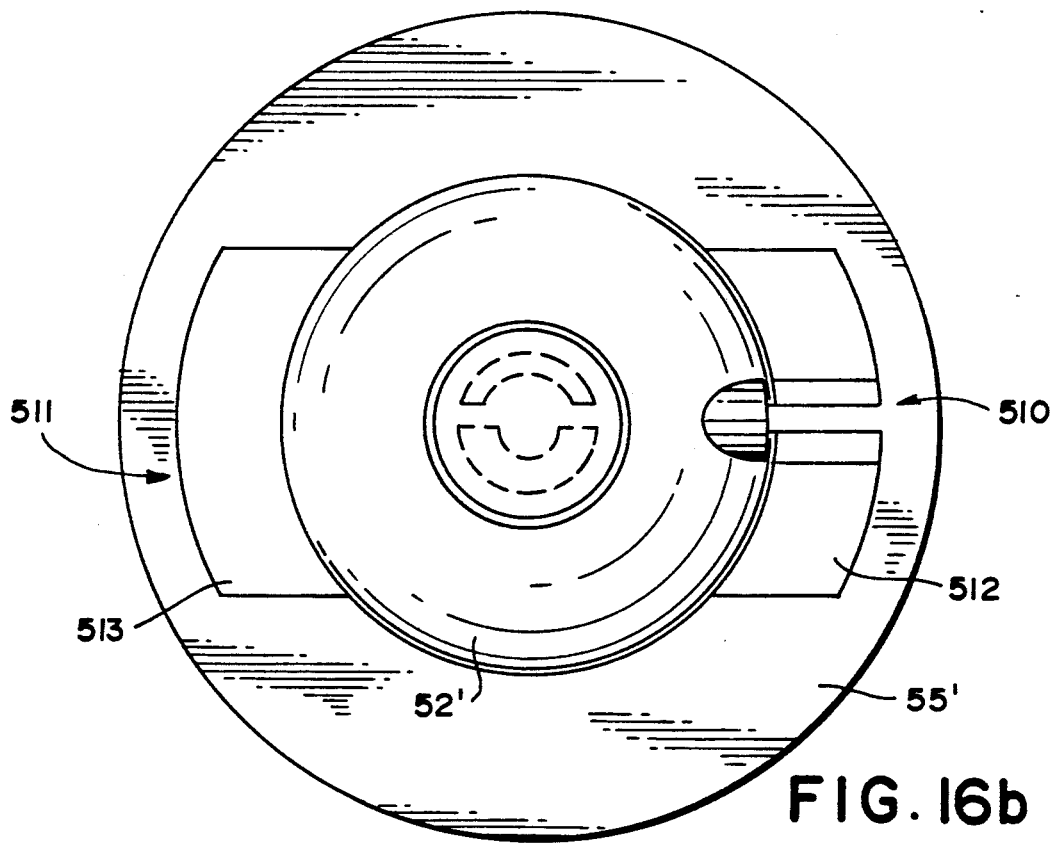

As shown in FIGS. 16a and 16b, the proximal end 510 of the detector 10' is considered to be that at which the lead lines 16 and 18 attach to the detector body and the opposite end is considered to be the distal end 511. Extending from the bowl-shaped portion 52' and formed as part thereof, are radially extending planes 512 and 513 at the proximal and distal ends 510 and 511, respectively. The radially extending planes 512 and 513 are provided for attaching a peal-away adhesive attachment member 55'. The peal-away attachment member 55' is circular in shape and is cut away in the center thereof to receive therein the bowl-shaped portion 52'. Moreover, the radially extending planes 512 and 514 act as surfaces to which the adhesive attachment member 55' adheres to with a peal-away backing 515 being removed therefrom at the corresponding portions of the attachment member 55'. The remaining surfaces of the attachment member 55' are covered by the peal-away backing 515. Similar to motion detector 10, a slit 54a' is provided for receiving the line cord 200' so as to be substantially flush with the bottom surface of the motion detector 10'. The motion detector 10' is mounted on the patient, either chest or leg, with the proximal end (that at which the lead lines are attached), above the distal end with respect to the body surface of the patient when vertical.

FIGS. 12-14 illustrate the mounting arrangement of the switches 12a, 12b and 12c. Switches 12a and 12c are mounted at approximately 15 degrees off a center line 508 which passes through a center point on the circuit board 30'. In addition, switches 12a and 12c are mounted at approximately 30 degrees with respect to the plane of the circuit board 30'. On the other hand, switch 12b is mounted at the center of the circuit board 30' at approximately a 10 degree angle of tilt with respect to vertical as shown in FIG. 13.

As shown in FIGS. 15a and 15b, each of the switches 12a, 12b and 12c are designed to close when the mercury ball Hg rolls to the position proximate the switch leads where the two contact members (FIG. 2) are located. Otherwise, the switch is open (FIG. 15b). This implies that the switches close when their respective lead lines are vertically below the remainder of the switch.

As a result of the mounting configuration described above, each of the switches 12a, 12b and 12c is provided for detecting a certain motion. Switch 12b, the center mounted switch, closes when the relative position of the detector 10' is such that the patient is leaning upwards slightly past vertical (actually, approximately 10 degrees past vertical where "vertical" is considered 90 degrees relative to plane of the circuit board 30'). It has been found that when mounted on the leg or chest of the patient, the person must lean forward just past vertical when rising up, either in bed or in the process of getting out of bed. Switches 12a and 12c also will close in such a position. However, as a result of their position relative to the circuit board 30', switches 12a and 12c will open should the patient roll over to either side to a sufficient degree that the switch 12b might close. This prevents a false alarm caused by the patient rolling to either side in bed. Whereas, without the switches 12a and 12c the switch 12b alone might close when a patient rolls over giving a false indication that the patient is up or out of bed, switches 12a and 12c, being connected in series, prevent closing the circuit which would otherwise actuate the alarm.

FIG. 17 illustrates the motion detectors 10 or 10' as connected to a conventional switched nurse calling system 518 which are commonly installed in hospitals. As shown in block diagram form, the calling system 518 generally comprises a block of patient bed interfaces 520₁-520ₙ and a remote nursing monitoring station 524 having a plurality of alarms 526₁-526ₙ (visual and/or audio), one for each patient. The motion detector 10 or 10' is attached appropriately to each patient and connected to the calling system at a corresponding patient bed interface 520₁-520ₙ via plug 20. Each motion detector device 10 or 10' will draw necessary power from the nurse call system circuitry at the patient's bedside.

In operation, making or closing of the mercury switch motion switch sensor circuit switch(es) of device 10 or 10' upon sensing of patient body movement preparatory to ambulation, and/or closure of the plunger switch detachment sensor circuit (140, 160, 180) will switch the nurse call on for the corresponding patient to illuminate and/or activate the associated alarm of 526₁-526ₙ. Because the nurse call circuit will not be resettable to off in an ordinary manner at the nurse's station 524, the persistence of the on state, which will last until the patient once again resumes or is placed in a supine posture or until the device is reattached, will indicate to the nurse that the patient is in the process of getting out of bed preparatory to ambulation and/or that the device has been removed or become detached from the patient.

The device of the present invention may conveniently be provided in versions for attachment to either the left or right lateral surface of the patient's body as may be necessary or dictated by the proximity and location of the nurse call circuit connection, simply by utilizing symmetrical "left" and "right" conductor layouts for circuit board 300, the other components being identical among the left and right side versions since the versions need differ only with respect to the symmetrical orientations of the mercury switches.

It will be readily appreciated that the above-described patient ambulation motion detector device according to the present invention is amenable to various modifications within the scope of the invention. For example, the mercury switch(es) might be configured with an arcuate or curved rather than a straight bulb or tube, to provide different response characteristics to motion about the horizontal datum. Accordingly, the scope of the present invention is intended to be limited only by the appended claims.

I claim:

1. A motion detector to be attached to a portion of a patient's body so as to signal impending ambulation of the patient, the motion detector comprising:

motion sensor circuit means including at least first, second and third switch means;

each switch means comprising portions defining an elongated chamber having first and second spaced ends and a longitudinal axis extending therebetween, a mercury ball contained within said chamber for gravitational movement between said first and second ends, and spaced electrical contacts disposed at said first end of said chamber, each switch means being closed when said first end of said chamber is below said second end such that said mercury ball conductively connects said contacts, and otherwise being open;

said first, second and third switch means being electrically connected in series whereby said motion sensor circuit means is completed to provide a signal of impending ambulation only when all of said first, second and third switch means are closed;

support means defining a first reference plane, and having a proximal end and a distal end, a first reference line on said first reference plane extending between said proximal and distal ends, and side portions laterally spaced from said first reference line;

attachment means for securing the motion detector to a portion of a patient's body with said proximal end of said support means proximal the patient's head relative to said distal end;

said first, second and third switch means being carried by said support means in a fixed three-dimensional configuration with respect to each other and with respect to said first reference plane;

said first switch means being fixedly carried by said support means with its longitudinal axis aligned with said first reference line and inclined with respect to said first reference plane, said second end of said first switch means being lower than said first end when said motion detector is in a first position wherein said first reference plane is generally horizontal, whereby said first switch means is open in said first position, and closed only when the motion detector is pivoted about said distal end of said support means from said generally horizontal first position to a second position wherein said proximal end of said support means is raised above said distal end past a predetermined threshold indicative of impending ambulation of the patient;

said second and third switch means being fixedly carried by said support means on opposite sides of said first reference line with their longitudinal axes inclined toward said first reference line, each of said second and third switch means having its first end lower than its second end when the motion detector is in said second position, one or the other of said second and third switch means having its second end lower than its first end when the motion detector is rotated about said first reference line to raise one side of said support means substantially above the other.

2. The motion detector of claim 1, and further comprising:
an insulated cord containing two electrical conductors connected to said support means in parallel with the series connected first, second and third switch means; and
a plug member attached at one end of said insulated cord for connecting the motion detector to a patient monitoring system.

3. The motion detector of claim 1, wherein each of said second and third switch means have its first end lower than its second end when the motion detector is in both said first and second positions.

4. The motion detector of claim 1, and further comprising housing means for housing said motion sensor circuit means and said support means, said attachment means being connected to a surface of said housing means.

5. The motion detector of claim 1, wherein said support means includes a substantially rigid support member having an upper and lower surface, said lower surface being juxtaposed to the portion of the patient's body in use, said first, second and third switch means being fixedly secured to the upper surface of said support member in said fixed three-dimensional configuration.

6. The motion detector of claim 5, wherein said first switch means is carried by said support member with its longitudinal axis inclined at approximately 100° relative the upper surface of the support member and the proximal end thereof.

7. The motion detector of claim 5, wherein said second and third switch means are carried by said support member with their longitudinal axes inclined at an angle of approximately 30° relative to the upper surface of the support member.

8. The motion detector of claim 7, wherein the axes of said second and third switch means are offset at an angle of approximately 15° with respect to a second reference line which extends substantially perpendicularly with respect to said first reference line on said first reference plane.

* * * * *